United States Patent [19]

Takano et al.

[11] Patent Number: 4,758,513

[45] Date of Patent: Jul. 19, 1988

[54] HUMAN T OR B CELL LINES AND A PROCESS FOR PRODUCING IMMUNOLOGICALLY ACTIVE SUBSTANCES USING THE SAME

[75] Inventors: Satoshi Takano, Yokohama; Hajimu Morioka, Kawasaki; Hiroshiro Shibai, Chigasaki; Kazukiyo Onodera, Tokyo, all of Japan

[73] Assignee: Ajinomoto Co., Inc., Tokyo, Japan

[21] Appl. No.: 736,376

[22] Filed: May 21, 1985

[30] Foreign Application Priority Data

May 21, 1984 [JP] Japan ................................. 59-102282

[51] Int. Cl.$^4$ ...................... C12N 5/00; C12P 21/00; C12R 1/91
[52] U.S. Cl. .................................. 435/68; 435/240.2; 435/948
[58] Field of Search ............... 435/240, 68, 948, 240.2

[56] References Cited

U.S. PATENT DOCUMENTS 4,560,655 12/1985 Baker ............................. 435/240 X

OTHER PUBLICATIONS

Takahashi et al., "Protein Synthesis in the Cells Transformed by Ela Gene of Adenovirus Type 12"; Growth Differ. Cells Defined Environ. Proc. Int. Symp. 1984, Pub. 1985, pp. 425–427.
Takahashi et al. *Chem Abstracts* 104:222739c 1986.
Takahashi et al. *Chem Abstracts* 103:17737p 1985.
Shiroki et al. *J. Virol* 45(3): 1074–82 1983.
Eager et al. *Proc Natl Acad Sci USA* 82:5525–5529 1985.
Schrier et al. *Nature* 305:771–775 1983.
Weeks et al. *Molec Cell Biol* 3(7):1222–1234 1983.
Pelham *Cell* 30:517–528 1982.

*Primary Examiner*—Elizabeth Weimar
*Attorney, Agent, or Firm*—Oblon, Fisher, Spivak, McClelland & Maier

[57] ABSTRACT

This invention relates to a human T or B cell line carrying at least one Ela human adenovirus 12-type gene or fragment thereof; said cell line being capable of spontaneously producing an immmunologically active substance. This invention also relates to a process for producing an immunologically active substance comprising culturing a human B- or T- cell line carrying at least one human Ela adenovirus 12-type gene or fragment thereof in a culture medium capable of supporting growth thereof for a period of time effective to attain a spontaneous production of the substance thereof.

6 Claims, 1 Drawing Sheet

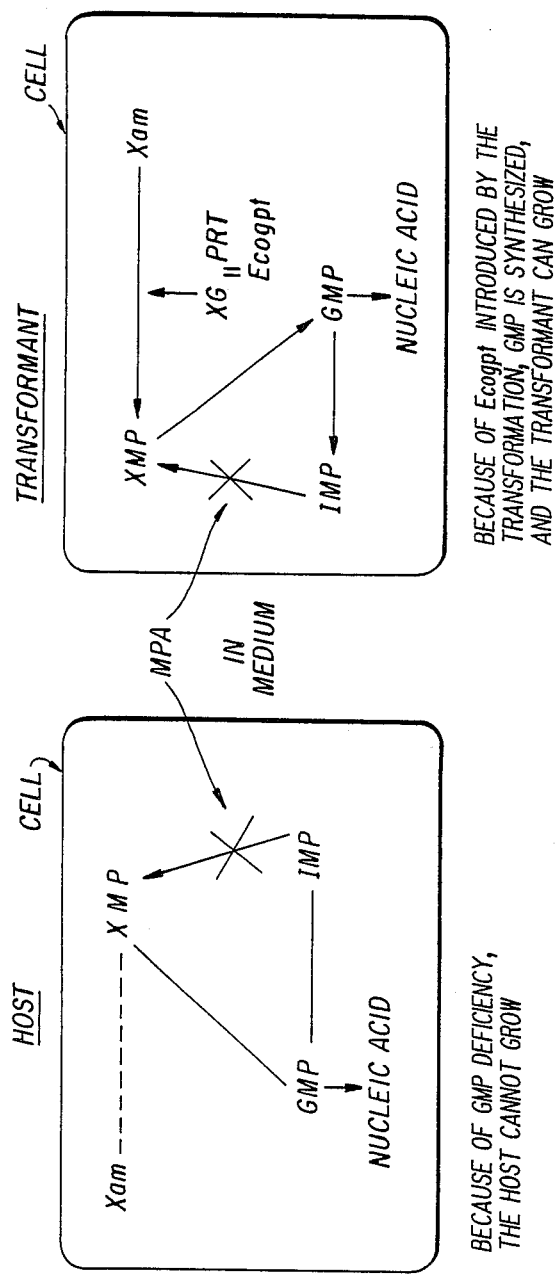

HUMAN T OR B CELL LINES AND A PROCESS FOR PRODUCING IMMUNOLOGICALLY ACTIVE SUBSTANCES USING THE SAME

BACKGROUND OF THE INVENTION

1. Field of the Invention

The present invention relates to improved human T or B cell lines and a process for producing immunologically active substances using the same.

2. Discussion of Background

It has heretofore been known that human T and B cell lines are stimulated by immunologically active substance inducers such as lectin, etc. to produce soluble, immunologically active substances such as $\alpha$-, $\beta$- or $\gamma$-interferons, interleukin-2, interleukin-1, B cell growth factor, CSF, etc. In most cases, however, these human T and B cell lines will not produce immunologically active substances unless they are stimulated by immunologically active substance inducers such as phorbol ester, lectin, etc. Accordingly, somewhat complicated operations such as adding inducers to the medium have been hitherto required for the production of immunologically active substances. However, the production of immunologically active substances through the addition or incorporation of inducers to the medium was not proven stable.

Furthermore, the productivity of immunologically active substances by conventional human T or B cell lines was not always satisfactory in the past.

SUMMARY OF THE INVENTION

This invention provides cells which spontaneously produce immunologically active substances with high efficiency and without requiring stimulation with inducers. The present cells produce the immunologically active substances in an extremely efficient manner.

More particularly, the present invention relates to improved human T and B cell lines carrying at least one E1a gene derived from human adenovirus 12-type and capable of producing an immunologically active substance. This invention also relates to a process for producing an immunologically active substance by culturing the cells disclosed herein.

DESCRIPTION OF THE DRAWING

FIG. 1: Scheme of host and transformant cell capability for synthesizing GMP.

DESCRIPTION OF THE INVENTION

The present inventors have succeeded in introducing human adenovirus 12-type derived E1a genes into human T or B cells, thus obtaining human T or B cell lines capable of spontaneously producing immunologically active substances.

The present invention concerns itself with improved human T or B cell lines carrying at least one E1a gene derived from human adenovirus 12-type, and a process for producing immunologically active substances using the cells thereof.

The human T or B cells useful in conjunction with the present invention include any type of human normal T or B cells and malignant T or B cells.

Normal human T cells such as human peripheral blood T cells may be utilized herein. In order to obtain normal human T cells, human peripheral blood may be treated using the ficoll gravity precipitation method to obtain lymphocytes. Human T cells can be obtained from the lymphocytes according to the E rosette method using sheep red cells and the like.

To obtain T cells from other tissues, e.g., tonsil tissue, the tissue is unfastened with tweezers in a medium such as RPMI-1640 medium, to obtain a cell suspension, from which lymphocytes are separated according to the ficoll gravity precipitation method. Human T cells can be obtained from lymphocytes according to the E rosette method, etc.

Examples of malignant human T cells include T cells isolated from T leukemic patients, T cells transformed by virus such as ATLV, HTLV, etc., fused cell lines of normal human T cells and myeloma cells or malignant T cells, cell lines obtained by transforming normal cells with drugs, radiation, etc.

Specific examples of malignant T cells include: CCRF-CEM (ATCC.CCL 119, Cancer, 18:522–529 (1965)); HPB-MLT (Int. J. Cancer, 21:166 (1978)); HPB-ALL (Int. J. Cancer, 21:166 (1977)); TALL (Nature, 267, 843 (1977)); RPMI-8402 (J. Natl. Cancer Inst., 55:11 (1975)), etc.

To obtain normal human B cells, any conventional method can be applied. For example, all methods described in "Techniques for Tissue Culture" edited by the Tissue Culture Association of Japan, can be used.

Specific examples of normal human B cells include RPMI 1788 (ATCC CCL-156), J. Nat. Cancer Inst., 43:1119 (1969).

As malignant human B cells for use in conjunction with this invention there can be mentioned those isolated from leukemic patients, those obtained by transformation of normal B cells with virus, cells exposed to drugs, radiation, and other methods to render them malignant as well as malignant T cells.

Specific examples include: CCRF-SB ((ATCC CCL-120-), Cancer Res. 27:2479 (1967)); Daudi ((ATCC CCL-213), Cancer Res. 28:1300 (1968)); IM-9 ((ATCC CCL-159), Ann. N.Y. Acad. Sci. 190:221 (1972)); Namalwa ((ATCC CRL-1432), J. Clin. Microbiol. 1:116 (1975)).

E1a genes derived from human adenovirus 12-type have the property of working upon other genes, thereby preventing the genes from expressing other genes (P. I. Schrier et al, Nature 305:771 (1983); D. L. Week et al, Mol. Cell. Biol. 3:1222 (1983);

Human adenovirus 12-type E1a genes for transduction can be obtained by culturing *E. coli* having the well known vector pSV$_2$-Ecogpt-E1a disclosed by J. Virology 45:1076 (1983) collecting the desired amounts of pSV$_2$-Ecogpt-E1a from the culture and separating the Ecogpt-E1a genes thereof by conventional methods ordinarily used in the art.

The Ad12 E1 gene is inserted into a transducing vector, pSV2-gpt, described by Mulligan and Berg, Science, 209, 1422–1427, and Mulligan and Berg, Proc. Natl. Acad. Sci. U.S.A. 78, 2072–2076, which is introduced into KB cells, and KB cell clones containing the *E. coli* gpt gene (Gpt+clones) may be isolated in a selective medium. Ad12 E1a genes may then be expressed by the clones containing the *E. coli* gpt gene. The plasmid DNA containing the E1a gene may be constructed by insertion of the E1a gene into a pSV2-gpt vector between the BamHI and EcoRI sites. Thereafter, the thus obtained genes are introduced into cells also by methods well known in the art, e.g., in accordance with the calcium-phosphate method, whereby both the gene Ecogpt and E1a gene are introduced into the cell.

The Ecogpt gene contains the gene coding for XGPRT. The following nomenclature will be used throughout this application.

XAN=xanthine
IMP=inosine-5'-monophosphate
XMP=xanthosine-5'-monophosphate
GMP=guanosine-5'-monophosphate
XGPRT=xanthine-phosphoribosyltransferase (or guanine)

Usually, Ecogpt-E1a is not cut between Ecogpt and E1a during the course of transformation and both of them are introduced together into the cells.

The selection of transformants is facilitated by incorporating mycophenolic acid (MPA) and xanthine into the selection medium. Mycophenolic acid inhibits the enzyme cycle from IMP to XMP in the GMP synthesis system. By the action of XGPRT activity of the cell having Ecogpt (and then E1a), GMP synthesis is effected from xanthine through XMP, whereby the growth of the transformed cells can be effected, while the non-transformed strains remain incapable of growing in the medium. Accordingly, only cells in which Ecogpt and the human adenovirus 12-type E1a genes have been introduced can grow (see, FIG. 1 of the attached drawing).

The presence of E1a genes can be confirmed by the Southern hybridization technique. Briefly, the Southern hybridization method comprises:

cleaving DNA fragments extracted from transformed cells by restriction enzyme digestion;

fractionating the DNA fragments on the basis of their size by means of agarose gel electrophoresis;

modifying double-stranded DNA fragments into single-stranded DNA fragments in an alkali solution; and then placing a nitrocellulose filter into close contact with the gel to transfer the modified DNA segments into the filter in the presence of a high salt concentration solution.

On the other hand, the E1a gene may be cleaved by DNase to generate a breakage site and then regenerated utilizing DNA polymerase I. When $^{32}P$-labelled nucleotide is used during the course of the experimental work, the resulting DNA segments are marked with radioactivity and may be utilized as a probe to detect complementary DNA fragments. The thus obtained probe is denatured by using heat to form single-stranded DNA fragments, followed by hybridization with a nitrocellulose filter having single-stranded DNA attached thereto and obtained from the aforesaid cells. The filter is rinsed and an autoradiogram is then obtained by contact thereof with a radioactivity sensitive film, whereby the E1a gene in the DNA fragments of the transduced cells is detected on an X-ray film in black.

The thus transduced cells can now be cultured again in a fresh medium containing neither mycophenolic acid nor xanthine and the medium or supernate of the culture and the cells can be examined for the appearance of immunologically active substances as indicated in the Examples.

A method for producing immunologically active substances using the thus obtained cells spontaneously producing an immunologically active substance is not particularly different from any conventional method for producing immunologically active substances using conventional cells having such capability. As media for culturing the cells of the present invention, there can be used, of course, serum-free media derived from conventional media, such as RITC 55-9 medium, RITC 56-1 medium, RITC 56-5 medium described in Published Unexamined Japanese Patent Application No. 74616/83, in addition to RPMI-1640 medium, among others.

A spinner flask, a roller bottle, an incubation tank with agitation and other suitable containers can be used for culturing the cells.

The immunologically active substances obtained from the cell culture (see, e.g., the Examples) may be used in the form of a supernate, depending upon their intended use. If necessary and/or desired, the immunologically active substances may be isolated from the culture supernate or cells and purified therefrom.

For the isolation and purification, various methods may be used, such as salting-out, concentration, vacuum dialysis, gel filtration, chromatrography, ion exchange chromatography, isoelectric point electrophoresis, gel electrophoresis and many others. These methods may be used singly or in an appropriate combination.

EXAMPLES

Example 1

The activity of interleukin 2 (IL-2) may be measured as follows. 100 μl of a sample or specimen are placed in the first line of a 96-well microtiter plate. A two-fold dilution is carried out with Dulbecco's modified Eagle medium (DMEM) containing 5% Fetal Bovine Serum (FBS) to prepare a serial dilution of 100 μl each on the 96-well microplate. Activated T lymphocytes prepared in accordance with the method disclosed by Gillis et al (Nature 268:154(1977)) to a concentration of $4 \times 10^3$ cell/100 μl are placed in each well. After culturing for 20 hours in an incubator containing 5% carbon dioxide in air at 37° C., 0.5 μCi of tritiated thymidine are added thereto followed by pulsing for 4 hours. The cells are then collected in a manner well known in the art and the radiation intake within the cells is measured. The higher the activity of IL-2 the culture supernatant has the larger is the tritiated thymidine intake into the activated T lymphocytes, from which the amount of IL-2 produced in the culture supernatant can easily be derived.

In this case, the amount of IL-2 produced in a solution containing Con A-stimulated (concanavalin A) rat spleen cells ($1 \times 10^6$ cell/ml of spleen cells, supplemented with 5 μg/ml of Con A, cultured for 48 hours) is defined to be 1 unit/ml, and the activity unit is calculated from the relative value (cf., Gillis et al, J. Immunol., 120:2027 (1978)).

EXAMPLE 2

The activity of IL-2 may also be measured as follows. The above-mentioned activated T lymphocyte culture is diluted in Dulbecco's modified Eagle's medium containing 5% FBS. 100 μl of a cell suspension thereof adjusted to 25 cell/well is placed in a 96-well microplate. Thereto, 100 μl of a sample or specimen are added, and incubation is conducted for 2 days in an atmosphere of air containing 5 vol % of carbon dioxide. Thereafter, the cells are counted. Since the higher the IL-2 activity is, the higher the activated T lymphocytes proliferate, the IL-2 productivity in the culture supernate can be noted.

EXAMPLE 3

The activity of, e.g., interferon, may be carried out as follows. Detroit 550 cells (ATCC CCL 109) are cultured in RPMI-1640 medium supplemented with 10% fetal bovine serum (FBS). The cultured cells are then suspended in a medium having the same composition as described above and $2\times10^4$ cells are seeded or inoculated per well in a 96-well microplate. This is followed by incubation for 3 days at 37° C. in an atmosphere of air containing 5 vol % carbon dioxide. The supernate is then removed. Thereto are added 100 μl each of a specimen previously prepared by serial dilution by repeated 5-fold dilution using RPMI-1640 medium containing 2% FBS. Incubation is carried out for one more day. After the supernate is removed, 100 μl of a suspension of vesicular stomatitis virus, which was previously adjusted with RPMI-1640 medium containing 2% FBS to a concentration exhibiting 50% inhibition, is added to cause infection in 20 to 24 hours. Cellular denaturation is observed and judged microscopically. The activity can be determined with reference to how the various interferon dilutions can prevent the "cellular denaturation effect" occurred when viral infection of the cells is effected. A dilution magnification at which the cellular denaturation effect is prevented by 50% is determined and the dilution magnification is taken as the interferon titer, Enders, J. F., et al., Proc. Natl. Acad. Sci. U.S. 45:385(1959)).

EXAMPLE 4

Cell culture may be conducted, e.g., as follows. The cells are suspended in RPMI-1640 medium plus from 2.5 to 10% FBS, so as to have an initial cell concentration of $1\times10^5$ cell/ml. The suspension is separately poured into a flask in an amount of 25 ml/flask (No. 3024, Falcon Co., Ltd.) and allowed to settle at 37° C. for 3 to 4 days in an atmosphere of air with 5 v/v % $CO_2$ for incubation. In the case of culturing the cells in a spinner flask, 175 ml of the suspension is charged in a spinner flask (No. 1967-00250, Belco Co., Ltd.) having a total volume of 600 ml at the above-mentioned cell concentration in the above-mentioned medium followed by incubation at 37° C. for 3 to 4 days at 50 to 150 r.p.m. A spinner flask (No. 1967-15000, Belco Co., Ltd.) having a total volume of 20 liters is used, 5 liters of a suspension consisting of the cells and the medium are charged therein followed by incubation at 37° C. for 3 to 4 days at 50 to 150 r.p.m. In the case of culturing the cells in a roller bottle (No. 3027, Falcon Co., Ltd., No. 3027), 500 ml of the suspension are charged therein at the above-mentioned cell concentration and under the above-mentioned medium conditions followed by roll-culturing (rotating the bottles) at 37° C. for 3 to 4 days at 2 to 30 r.p.m.

EXAMPLE 5

The above culture supernate is filtered through a filter of 0.45 micron and ammonium sulfate is gradually added to reach 50% saturation. After agitating for 1 hour, the mixture is then centrifuged for 10 minutes at 10,000 x g to recover the supernate. Ammonium sulfate is supplemented to the supernate to reach 75% saturation. After allowing to stand for 2 hours, the mixture is again centrifuged for 20 minutes at 10,000 x g. The resulting precipitate is dissolved in 0.01 M Tris-HCl buffer, pH 7.4. The solution is dialyzed against the same buffer for 48 hours and the dialysate is developed onto a DEAE Sepharose column which was previously equilibrated with 0.01 M Tris-HCl buffer, pH 7.4, followed by gradient elution using the same buffer and 0.1 M saline solution. The immunologically active substances are present in the fractions eluted at a salt concentration of about 0.07 M. The fractions are then collected and 10% polyethylene glycol (PEG-6000, Wako Junyaku Co., Ltd.) is added to a concentration of 1%. The mixture is concentrated using a Diaflow YM 5 membrane (Amicon Co., Ltd.). The thus obtained concentrate is developed onto a Sephadex 150 column (Pharmacia Col, Ltd.), which is eluted with phosphate-buffered physiological saline solution containing 0.1% PEG. The fractions containing the immunologically active substance are collected and a 10% PEG solution is again added thereto. The mixture is then concentrated with a Diaflow YM 5 membrane to obtain a purified specimen.

Immunologically active substances can be produced by using the improved human T or B cell lines of the present invention without adding any inducers to the media. Further, immunologically active substances can be produced with higher efficiency by culturing the improved human T or B cell lines of the present invention. The immunologically active substances which can be produced in accordance with the process of the present invention include interleukin-1, -2 and -3, interferon-$\alpha$, -$\beta$ and -$\gamma$, CSF, BCGF, etc.

EXAMPLE 6

*E coli* having incorporated therein the pSV$_2$-Ecogpt-E1a gene (J. Virology 45:1074 (1983)) was cultured at 37° C. for 18 hours in 10 ml of L-broth supplemented with 50 μg/ml ampicillin. The culture was then transferred to 1 liter of a medium having the same composition described above and cell culturing was continued for 4 more hours using a rotary flask having a total volume of 5 liters. Thereafter, chloramphenicol was added to a concentration of 170 μg/ml and culturing continued for 18 more hours. The thus obtained culture supernate was centrifuged at 5,000 x g for 10 minutes at 4° C. to harvest the cells. After washing the cells with 50 mM Tris-HCl buffer, pH 8.0, and 5 mM EDTA buffer, the cells were resuspended in the aforesaid EDTA buffer containing in addition 25% sucrose to a volume of 15 ml per 3 g of the cells. 30 mg of lysozyme were then added to the suspension and the cells were treated at 0° C. for 20 minutes to obtain spheroplasts. 100 mM Tris-HCl buffer, pH 8.5, containing 0.5% Triton X 100 and 15 ml of 100 mM EDTA solution were added to the resulting spheroplasts. After maintaining the mixture at 0° C. for 15 minutes, the mixture was centrifuged at 28,000 x g for 30 minutes at 4° C. and the supernate separated thereof. After adjusting the refractivity of the thus obtained supernate to 1.395 by adding cesium chloride thereto, DNA was recovered by centrifuging for 40 hours at 40,000 x g. After decolorizing with isoamyl alcohol, calcium chloride was removed by dialysis. The plasmid pSV$_2$-Ecogpt-E1a was then obtained by ethanol pecipitation. The thus obtained plasmid was used to transform a Jurkat-MT strain by the calcium phosphate method which is well known in the art.

The Jurkat-MT strain used herein was obtained as follows. Jurkat-FHCRC strain cells (Gillis, S., et al, J. Exp. Med. 152:1709(1980)) were obtained by cultivating in RPMI-1640 medium containing 10% fetal bovine serum (FBS). The cells were then suspended in fresh RPMI-1640 +10% FBS medium at a concentration of $1\times10^5$ cell/ml. In a plastic dish (No. 1007, Falcon Co., Ltd.) 5 ml of the suspension were placed and N-methyl-N'-nitro-N-nitrosoguanidine was added thereto to a final concentration of 1.5 μg/ml. After culturing at 37°

C. for 16 hours in an atmosphere of air containing 5 v/v % $CO_2$, the cells were harvested by centrifugation followed by washing with physiological saline twice or thrice. An initial cell concentration of $1 \times 10^5$ cells/ml was obtained, again using fresh RPMI-1640+10% FBS medium, 25 ml of which were placed in a flask (No. 3024, Falcon Co., Ltd.) and cultured at 37° C. for 4 days in an atmosphere of 5 v/v % $CO_2$ in air. The initial concentration of the thus mutated cells was adjusted to $1 \times 10^5$ cells/ml using fresh RPMI-1640 5% FBS medium, placed in a 96-well microtiter plate (Falcon Co., Ltd.) and cultured at 37° C. for 4 days in an atmosphere of 5 v/v % $CO_2$ in air. The cell count was obtained and a strain which grew to the level of $1 \times 10^6$ cells/ml was separated as Jurkat-MT.

Transformation was performed by mixing 200 μg of the obtained DNA plasmids with 2.5 ml of a 125 mM calcium chloride solution, gently adding the resulting liquid to 25 ml of phosphate buffer (Shen, Y. M., et al, Mol. Cell. Biol. 2:1145(1982)) and the mixture was allowed to react at 37° C. for 1 hour. To the reaction mixture were added $1 \times 10^7$ cells of the parent Jurkat-MT strain cultured using RPMI-1640 medium containing 2.5% FBS, followed by cultivation at 37° C. for 1 hour. The cells were then suspended in a medium having the same composition described above to a final concentration of $1 \times 10^5$ cell/ml, and 2 ml each of the suspension were placed in a 24 well-plate (No. 3047, Falcon Co., Ltd.). After culturing at 37° C. for 24 hours in an atmosphere of air containing 5 v/v % $CO_2$, 2 ml of a fresh medium having the same composition described above were exchanged for the old medium in the wells. Cultivation was then continued at 37° C. for 3 days in an atmosphere of air containing 5 v/v % $CO_2$.

From the thus transformed cells, the desired cells were obtained by the following method. Cell cultivation was performed in RPMI-1640 medium containing 0.5 μg/ml mycophenolic acid, 250 μg/ml xanthine and 2.5% FBS, at 37° C. for 2 to 3 weeks in an atmosphere of air containing 5 v/v % $CO_2$. During this time one half of the culture liquid was exchanged anywhere from every other day to every four days, whereby the 32 cell lines grown were harvested. The incorporation of the E1a gene in the thus obtained cell lines was confirmed by the Southern hybridization method. The initial concentration of the cells was then adjusted to $1 \times 10^5$ cell/ml using fresh RPMI-1640 medium containing 2.5% FBS, and 25 ml of which were placed in a flask (No. 3024, Falcon Co., Ltd.) and cultured at 37° C. for 4 days in an atmosphere of air containing 5 vol % $CO_2$. The production of human IL-2 in the culture supernate was then determined by the method described above using the proliferation of activated T lymphocytes as a measure of human IL-2 productivity. As shown in Table 1, Jurkat-MTE 20, -MTE 22, -MTE 23, -MTE 26 and -MTE 31 cells, which constitutively produce human IL-2, were obtained.

TABLE 1

| Cell | Human IL-2 Productivity (cell count of activated T Lymphocyte) | | |
|---|---|---|---|
| Jurkat-MT | 1, | 5, | 0, |
| Jurkat-MTE 20 | 60, | 71, | 90, |
| Jurkat-MTE 22 | 64, | 66, | 63, |
| Jurkat-MTE 23 | 117, | 102, | 106, |
| Jurkat-MTE 26 | 48, | 61, | 78, |
| Jurkat-MTE 31 | 86, | 55, | 69, |

EXAMPLE 7

Cells from the cell line Jurkat-MET 31 obtained in Example 6 were adjusted with RPMI-1640 medium to an initial concentration of $1 \times 10^5$ cell/ml, and 25 ml thereof were placed in a flask (No. 3024, Falcon Co., Ltd.). After culturing at 37° C. for 3 days in an atmosphere of air containing 5 v/v % of carbon dioxide, the solution was diluted to 2.5 cells/ml using a medium having the same composition described above and 200 μl each of the diluted preparation were placed in a 96-well microplate (No. 3072, Falcon Co., Ltd.). This was followed by incubation at 37° C. for 2 weeks in an atmosphere of air containing 5 v/v % of carbon dioxide. The 62 cell lines which were grown from the thus incubated 96-well plate were harvested. The thus obtained cells were adjusted with RPMI-1640 medium containing 2.5% FBS to an initial cell concentration of $1 \times 10^5$ cells/ml, and 25 ml thereof were placed in a flask (No. 3024, Falcon Co., Ltd.), followed by incubation at 37° C. for 3 days in an atmosphere of air containing 5 v/v % carbon dioxide. The thus cultured cells were adjusted with RPMI-1640 medium containing 1% FBS to an initial cell concentration of $2 \times 10^6$ cell/ml. Thereafter, con A which is a human IL-2 production-inducing agent was added to a concentration of 50 μg/ml. 175 ml of the mixture were charged into a spinner flask (No. 1967-00250, Belco Co., Ltd.) and the cells were cultured at 37° C. for 24 hours at 50 to 150 r.p.m. The production of human IL-2 in the culture supernate was measured as the intake of tritiated thymidine using activated T lymphocytes as described hereinabove. Two cell lines (Jurkat-MTE 31-12 and Jurkat-MTE-31-45) evidencing higher human IL-2 productivity than the parent cells were obtained. The results are shown in Table 2.

TABLE 2

| Cells With High IL-2 Productivity | |
|---|---|
| Cell | Human IL-2 Productivity (unit/ml) |
| Jurkat-MT | 3160 |
| Jurkat-MTE-31-12 | 22000 |
| Jurkat-MTE-31-45 | 13500 |

EXAMPLE 8

In a manner similar to Example 6, the E1a gene was transduced into Namalwa cells (obtained from the Frederick Cancer Research Center, MD, U.S.A.) cultured in RPMI-1640 medium containing 10% FBS. The cells were subjected to transduction using as a selection medium a 10% FBS-containing RPMI-1640 medium supplemented with 5 μg/ml mycophenolic acid and 250 μg/ml xanthine and the desired 25 cell lines were obtained. The thus obtained cells were adjusted with 10% FBS-containing RPMI-1640 medium to an initial cell concentration of $1 \times 10^5$ cell/ml and 25 ml of cells were placed in a flask (No. 3024, Falcon Co., Ltd.), and incubated at 37° C. for 3 to 4 days in an atmosphere of air containing 5 v/v % carbon dioxide. The production of IFN in the culture supernate was determined by measuring human IFN activity as described hereinabove. The results are described in Table 3 below, wherein the productivities of each of 3 cell lines spontaneously producing human IFN are compared with the parent Namalwa cell line lacking a transduced E1a gene.

TABLE 3

| Cell | Human IFN Productivity | |
|---|---|---|
| | E1a Transduction | Human IFN Productivity (μ/ml) |
| Namalwa strain | − | 2 |
| Namalwa strain No. 7 | + | 20–30 |
| Namalwa strain No. 25 | + | 40–50 |
| Namalwa strain No. 28 | + | 30–40 |

EXAMPLE 9

Cells from the Namalwa cell line No. 25 obtained in Example 8 into which an E1a gene was transduced were adjusted with a 10% FBS-containing RPMI-1640 medium to an initial cell concentration of $1 \times 10^5$ cell/ml. 175 ml of the cell suspension were placed in a spinner flask (No. 1967-00250, Belco Co., Ltd.), and incubation was carried out for 3 to 4 days at 50 to 100 r.p.m. and 37° C. To the culture was added New Castle disease virus to attain an erythrocyte agglutination activity of 4 units/$1 \times 10^5$ cells. After culturing for 20 to 30 hours at 35° C. and 100 to 200 r.p.m., the reaction mixture was centrifuged for 10 minutes at 5000 r.p.m. to separate the supernate. The production of human IFN in the supernate was then determined by measuring human IFN activity as described hereinabove. The results are described in Table 4 as a comparison with the parent Namalwa cells carrying no transduced E1a gene.

TABLE 4

| Cell | Human Interferon Production | |
|---|---|---|
| | E1a Transduction | Human IFN Productivity |
| Namalwa cell line | − | 4400 μ/ml |
| Namalwa cell 25 | + | 13500 μ/ml |

Sample embodiments of the invention identified as Jurkat-MTE-23 and Jurkat-MTE-31-12 have been deposited at the Institute for Fermentation Osaka (IFO), Osaka, Japan, in the accession numbers of IFO 50052 and IFO 50053, respectively. Samples of the same cell lines were transmitted to the Plum Island Animal Disease Center for safety testing on March 7, 1985, to obtain a license to send them for deposit to the American Type Culture Collection, Rockville, Md.

What is claimed as new and desired to be secured by letters patent of the United States is:

1. A human T or B cell line selected from the group consisting of Jurkat cells and Namalwa cells carrying at least one E1a Human adenovirus 12-type gene; said cell line being capable of constitutively producing an immunologically active substance selected from the group consisting of α-, β- or γ-interferon, interleukin-2, interleukin-1, B cell growth factor and CSF.

2. The cell line of claim 1, which is Jurkat-MTE-31-12.

3. The cell line of claim 1, which is Jurkat-MTE-23.

4. The cell line of claim 1, which is a Namalwa cell.

5. A process for producing an immunologically active substance comprising culturing a human B- or T-cell line selected from the group consisting of Jurkat cells and Namalwa cells carrying at least one human E1a adenovirus 12-type gene, in a culture medium capable of supporting growth thereof for a period of time effective to attain constitutive production of the substance thereof, wherein said substance is selected from the group consisting of α-, β- or γ-interferon, interleukin-2, interleukin-1, B cell growth factor and CSF.

6. A process according to claim 5, wherein said cell line is selected from the group consisting of Jurkat-MTE-23 and Jurkat-MTE-31-12.

* * * * *

UNITED STATES PATENT AND TRADEMARK OFFICE
CERTIFICATE OF CORRECTION

PATENT NO. : 4,758,513
DATED : JULY 19, 1988
INVENTOR(S) : SATOSHI TAKANO ET AL

It is certified that error appears in the above-identified patent and that said Letters Patent is hereby corrected as shown below:

In the ABSTRACT, line 4, delete "immmunologically" and insert --immunologically--.

Column 2, line 27, delete "RPMI 1788" and insert --RPMI-1788--;

line 37, delete "120-)," and insert --120),--;

line 46, delete "(1983);" and insert --(1983).--;

line 50, delete "(1983)" and insert --(1983),--;

line 54, delete "E1 gene" and insert --E1a gene--;

line 55, delete "pSV2-gpt" and insert --$pSV_2$-gpt--;

line 63, delete "pSV2-gpt" and insert --$pSV_2$-gpt--.

Column 4, line 24, delete "interleukin 2" and insert --interleukin-2--;

line 54, delete "Eagle's" and insert --Eagle--;

line 67, delete "(ATCC CCL 109)" and insert --(ATCC CCL-109)--.

UNITED STATES PATENT AND TRADEMARK OFFICE
CERTIFICATE OF CORRECTION

PATENT NO. : 4,758,513
DATED : JULY 19, 1988
INVENTOR(S) : SATOSHI TAKANO ET AL

It is certified that error appears in the above-identified patent and that said Letters Patent is hereby corrected as shown below:

Column 6, line 26, delete "E coli" and insert --E. coli--;

line 55, delete "pecipitation" and insert --precipitation--.

Signed and Sealed this

Twenty-fifth Day of July, 1989

Attest:

DONALD J. QUIGG

Attesting Officer

Commissioner of Patents and Trademarks